United States Patent
Opperman et al.

(10) Patent No.: US 9,750,915 B2
(45) Date of Patent: Sep. 5, 2017

(54) NASAL CANNULA COMFORT TIP

(71) Applicants: David A. Opperman, Littleton, CO (US); Robert Witkow, Englewood, CO (US)

(72) Inventors: David A. Opperman, Littleton, CO (US); Robert Witkow, Englewood, CO (US)

( * ) Notice: Subject to any disclaimer, the term of this patent is extended or adjusted under 35 U.S.C. 154(b) by 762 days.

(21) Appl. No.: 13/910,418

(22) Filed: Jun. 5, 2013

(65) Prior Publication Data
US 2013/0333705 A1 Dec. 19, 2013

Related U.S. Application Data

(60) Provisional application No. 61/661,489, filed on Jun. 19, 2012.

(51) Int. Cl.
| | |
|---|---|
| *A62B 9/02* | (2006.01) |
| *A62B 9/06* | (2006.01) |
| *A61M 16/00* | (2006.01) |
| *A61M 16/06* | (2006.01) |
| *A61M 16/16* | (2006.01) |

(52) U.S. Cl.
CPC .... *A61M 16/0666* (2013.01); *A61M 16/0672* (2014.02); *A61M 16/16* (2013.01); *A61M 2202/0208* (2013.01)

(58) Field of Classification Search
None
See application file for complete search history.

(56) References Cited

U.S. PATENT DOCUMENTS

| | | | | |
|---|---|---|---|---|
| 718,785 | A * | 1/1903 | McNary | A61M 16/0666 128/207.18 |
| 4,267,831 | A * | 5/1981 | Aguilar | A61M 15/085 128/203.14 |
| 4,648,398 | A * | 3/1987 | Agdanowski et al. | 128/207.18 |
| 4,915,105 | A * | 4/1990 | Lee | A62B 18/00 128/205.27 |
| 6,354,293 | B1 * | 3/2002 | Madison | A61M 16/0666 128/204.13 |
| 6,994,089 | B2 * | 2/2006 | Wood | A61M 16/0666 128/206.11 |
| 8,707,950 | B1 * | 4/2014 | Rubin | A61M 16/06 128/200.24 |
| 2005/0072430 | A1 * | 4/2005 | Djupesland | A61M 15/0091 128/206.11 |
| 2008/0060649 | A1 * | 3/2008 | Veliss | A61M 16/06 128/205.25 |
| 2008/0215002 | A1 * | 9/2008 | Rozenberg | A61F 7/123 604/113 |
| 2009/0032026 | A1 * | 2/2009 | Price et al. | 128/207.11 |
| 2009/0281482 | A1 * | 11/2009 | Baker | A61M 1/0058 604/28 |
| 2009/0308398 | A1 * | 12/2009 | Ferdinand | A61M 15/08 128/207.18 |
| 2010/0000534 | A1 * | 1/2010 | Kooij et al. | 128/204.18 |

(Continued)

*Primary Examiner* — Tan-Uyen (Jackie) T Ho
*Assistant Examiner* — Eric Bryant
(74) *Attorney, Agent, or Firm* — Alpine Technology Law Group LLC

(57) ABSTRACT

According to one embodiment, a device is disclosed. The device includes a nasal cannula having prongs to supply air and covers inserted over the prongs to prevent discomfort during use of the nasal cannula.

15 Claims, 1 Drawing Sheet

(56) References Cited

U.S. PATENT DOCUMENTS

| | | | |
|---|---|---|---|
| 2010/0018534 A1* | 1/2010 | Veliss | A61M 16/06 128/206.24 |
| 2010/0211140 A1* | 8/2010 | Barbut | A61F 7/12 607/105 |
| 2011/0048430 A1* | 3/2011 | Arnon | A24F 47/00 128/848 |
| 2011/0209701 A1* | 9/2011 | Derringer | A61M 16/06 128/202.17 |
| 2012/0305000 A1* | 12/2012 | Janka et al. | 128/205.25 |

\* cited by examiner

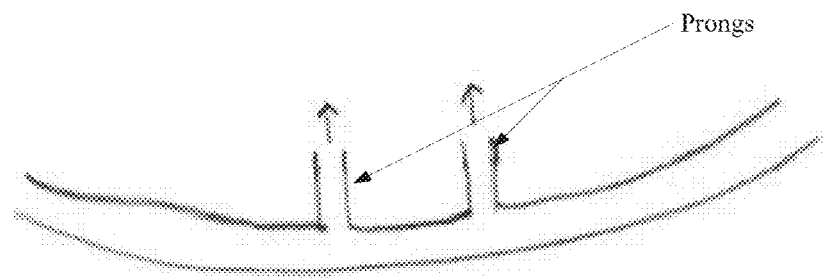
**Figure 1
(PRIOR ART)**
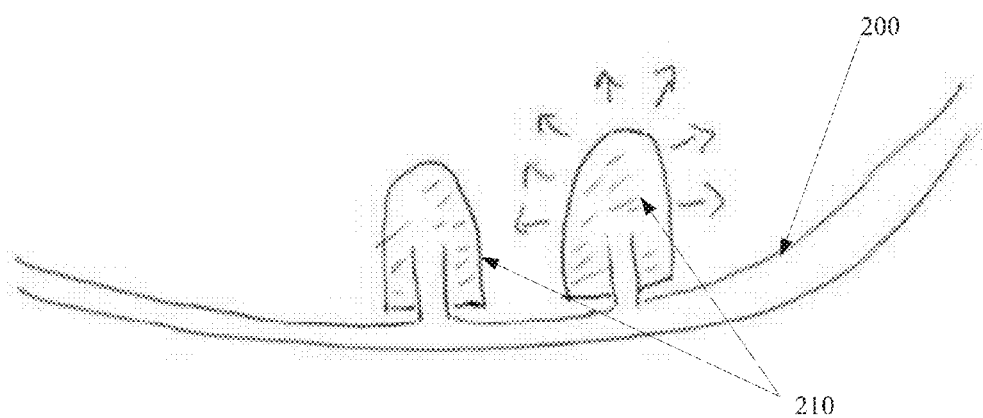
Figure 2
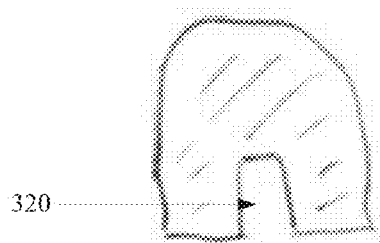 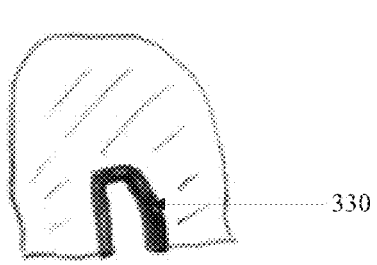
Figure 3A     Figure 3B

NASAL CANNULA COMFORT TIP

This is a non provisional application based on provisional application Ser. No. 61/661,489 filed on Jun. 19, 2012 and claims priority thereof.

FIELD OF THE INVENTION

The present invention relates to medical devices, more particularly, Nasal Cannula devices.

BACKGROUND

A nasal cannula is a device used to deliver supplemental oxygen or airflow to a patient or person in need of respiratory assistance. FIG. 1 illustrates one embodiment of a nasal cannula. The nasal cannula comprises a lightweight tube in which on one end splits into two prongs that are placed in the nostrils and from which a mixture of air and oxygen flows. The other end of the tube (not shown) is connected to an oxygen supply such as a portable oxygen generator, or a wall connection in a hospital via a flow meter. The cannula is generally attached to the patient by way of the tube hooking around the patient's ears or by elastic head band.

A problem with the existing nasal cannula design is that the prongs are often uncomfortable and may irritate the patient after extended or prolonged use. Specifically, the plastic material, of which the cannula is comprised, may scratch and or rub the skin of a user's nostrils, resulting in a skin rash or cut. Moreover, the prong tips focus the flow of oxygen, which causes drying of nasal tissue, which in turn causes nose bleeds.

Accordingly, a comfort tip for a nasal cannula is desired.

BRIEF DESCRIPTION OF THE DRAWINGS

The present invention will be understood more fully from the detailed description given below and from the accompanying drawings of various embodiments of the invention. The drawings, however, should not be taken to limit the invention to the specific embodiments, but are for explanation and understanding only.

FIG. 1 illustrates an exemplary nasal cannula;

FIG. 2 illustrates one embodiment of a nasal cannula having comfort tips; and

FIGS. 3A & 3B illustrate embodiments of a comfort tip a front.

DETAILED DESCRIPTION

A nasal cannula comfort tip is described. Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

In the following description, numerous details are set forth. It will be apparent, however, to one skilled in the art, that the present invention may be practiced without these specific details. In other instances, well-known structures and devices are shown in block diagram form, rather than in detail, in order to avoid obscuring the present invention.

FIG. 2 illustrates one embodiment of a nasal cannula 200. As shown in FIG. 2, comfort tips 210 cover the prongs of nasal cannula 200. Comfort tips 210 are foam covers that are inserted over the tip of the cannula 200 prongs. In one embodiment, the foam material provides tension to hold a comfort tip 210 on to the prongs. In a further embodiment, each foam cover is shaped to fit and open the nasal passages of a user. For instance, the foam may push open narrow nasal passage of a user.

In one embodiment, comfort tips 210 are sufficiently porous to diffuse air (e.g., oxygen) exiting from the prongs such as to not to interfere with the air flow. Specifically, comfort tips 210 diffuse oxygen in order to prevent oxygen from rushing out of the prongs. Direct oxygen flow from the cannula is delivered under pressure and passed through the foam. The basic properties of the foam distributes the oxygen through numerous cells and openings. According to one embodiment, the foam is configured to have little or no resistance (e.g., not too dense so as to block the flow of oxygen).

FIGS. 3A & 3B illustrate embodiments of a comfort tip 210. FIG. 3A illustrates one embodiment of a comfort tip 210. As discussed above, comfort tip 210 is shaped to gently expand a user's nasal passage to improve breathing. Thus, a possibility of continuous positive airway pressure (CPAP) is eliminated. In a further embodiment, comfort tip 210 is impregnated with lubricating gel. In such an embodiment, the lubricating gel may be a saline gel, or other material, that will increase comfort for the nasal cannula 200 user, as well as provide humidification.

Comfort tip 210 includes hole 320. In one embodiment, hole 320 has a diameter that is slightly smaller than the tip of a prong to enable compression of the foam to hold comfort tip 210 on to the cannula 200 prong. Thus, a comfort tip 210 is attached to nasal cannula 200 in a secure manner such that the comfort tip 210 will not be detached during regular use.

FIG. 3B illustrates another embodiment of a comfort tip 210 in which an insert 330 is inserted in hole 320. In such an embodiment, insert 330 may be comprised of a firmer material that is shaped to attach to so the cannula 200 prong. In one embodiment, insert 300 may snap on to the prong. However in other embodiments, insert 330 may screw on to the prong. In still other embodiments, hole 320 may be lined with any material that facilitates firm attachment, (e.g., plastic or rubber).

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims, which in themselves recite only those features regarded as the invention.

What is claimed is:

1. A device comprising:
    a nasal cannula having prongs to supply air; and
    foam covers inserted over the prongs to diffuse air exiting from the prongs in order to prevent discomfort during use of the nasal cannula, wherein the foam covers are impregnated with lubricating gel to humidify the diffused air.

2. The device of claim 1 wherein foam on the foam covers provides tension to hold the foam covers on to the prongs.

3. The device of claim 1 wherein the foam covers are shaped to fit and open nasal passages.

4. The device of claim 1 wherein the lubricating gel is a saline gel.

5. The device of claim 1 wherein the covers comprise a hole to fit over the prongs.

6. The device of claim 5 wherein the hole has a diameter smaller than a tip of a prong to enable compression of the foam to hold a cover on to a prong.

7. The device of claim 5 wherein the foam covers each comprise inserts within the hole to hold the foam covers on to the prongs.

8. The device of claim 7 wherein the inserts snap to the prongs.

9. The device of claim 7 wherein the inserts are screwed on to the prongs.

10. A device comprising foam covers inserted over nasal cannula prongs to diffuse air exiting from the prongs in order to prevent discomfort during use of the nasal cannula, wherein the foam covers are impregnated with lubricating gel to humidify the diffused air.

11. The device of claim 10 wherein the lubricating gel is a saline gel.

12. The device of claim 10 wherein the foam covers comprise a hole to fit over the prongs.

13. The device of claim 12 wherein a hole has a diameter smaller than a tip of a prong to enable compression of the foam to hold a cover on to a prong.

14. The device of claim 12 wherein the foam covers each comprise inserts attached within the hole to hold the foam covers on to the prongs.

15. The device of claim 14 wherein the inserts snap to the prongs.

* * * * *